(12) United States Patent
Fujimoto

(10) Patent No.: US 7,213,468 B2
(45) Date of Patent: May 8, 2007

(54) ULTRASONIC APPARATUS AND METHOD FOR MEASURING THE CONCENTRATION AND FLOW RATE OF GAS

(75) Inventor: Naotoshi Fujimoto, Hino (JP)

(73) Assignee: Teijin Pharma Limited, Tokyo (JP)

( * ) Notice: Subject to any disclaimer, the term of this patent is extended or adjusted under 35 U.S.C. 154(b) by 30 days.

(21) Appl. No.: 10/550,687

(22) PCT Filed: Apr. 20, 2004

(86) PCT No.: PCT/JP2004/005590

§ 371 (c)(1),
(2), (4) Date: Sep. 26, 2005

(87) PCT Pub. No.: WO2004/094960

PCT Pub. Date: Nov. 4, 2004

(65) Prior Publication Data

US 2006/0185443 A1    Aug. 24, 2006

(30) Foreign Application Priority Data

Apr. 21, 2003  (JP) ............... 2003-115333
Jun. 13, 2003  (JP) ............... 2003-168911
Jul. 8, 2003   (JP) ............... 2003-271779

(51) Int. Cl.
$G01F\ 1/66$     (2006.01)
(52) U.S. Cl. ................... 73/861.27; 702/48
(58) Field of Classification Search ............ None
See application file for complete search history.

(56) References Cited

U.S. PATENT DOCUMENTS 4,325,262 A    4/1982  Meisser et al.
5,052,230 A   10/1991  Lang et al.
5,123,286 A    6/1992  Baumgärtner
5,583,301 A *  12/1996  Strauss et al. ........... 73/861.29

FOREIGN PATENT DOCUMENTS

| EP | 0 606 536 A  | 7/1994  |
| EP | 1 286 159 A1 | 2/2003  |
| FR | 2 462 837 A  | 2/1981  |
| JP | 57-190281 A  | 11/1982 |

OTHER PUBLICATIONS

International Search Report (5 pages) mailed on Apr. 26, 2005.

* cited by examiner

*Primary Examiner*—Harshad Patel
(74) *Attorney, Agent, or Firm*—Rader, Fishman & Grauer PLLC

(57) ABSTRACT

An ultrasonic apparatus measures the concentration and flow rate of a sample gas by calculating a possible propagation time range on the basis of the gas temperature, determining whether or not the phases at which two first trigger signals, respectively generated on the basis of forward and backward waveforms of the ultrasonic waves, coincide with each other, processing the zero-cross signals so that the phases coincide with each other, obtaining reference zero-cross time instant by calculating mean value of the forward and backward zero-cross time instants, obtaining an ultrasonic reception point by subtracting an integral multiple of the cycle of the ultrasonic waves so that the results of the subtraction falls into a possible propagation time range and estimating the ultrasonic propagation time on the basis of the ultrasonic reception point.

22 Claims, 13 Drawing Sheets

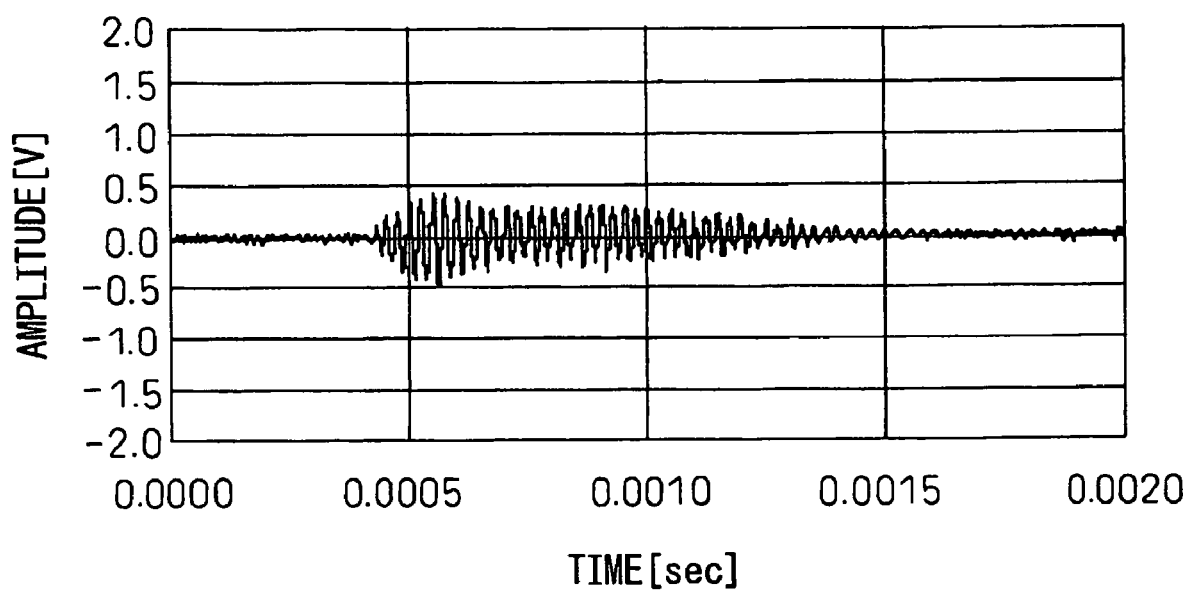

ULTRASONIC APPARATUS AND METHOD FOR MEASURING THE CONCENTRATION AND FLOW RATE OF GAS

TECHNICAL FIELD

The invention relates to ultrasonic apparatus and method for measuring the concentration of oxygen gas in a sample gas and flow rate of the sample gas, which is supplied from an oxygen concentrator used for a medical purpose.

BACKGROUND ART

It is well known that the propagation velocity of ultrasonic waves through a sample gas is presented by a function of the concentration and the temperature of the sample gas. The velocity C(m/sec) of ultrasonic waves propagating through a stationary gas is presented by flowing equation (1) with mean molecular weight M and the temperature T(K).

$$C = (\kappa RT/M)^{1/2} \quad (1)$$

Where:
κ: ratio of molecular specific heat at constant volume and molecular specific heat at constant pressure
R: gas constant Therefore, measuring the velocity of ultrasonic waves C(m/sec) propagating through a sample gas and the temperature T(K) of the sample gas will provide the mean molecular weight M of the sample gas through a calculation. For example, the mean molecular weight M of a sample gas containing an oxygen-nitrogen gas mixture of a mixture ratio P:(1−P) (0≦P≦1) will be calculated by following equation (2).

$$M = M_{O2}P + M_{N2}(1-P) \quad (2)$$

Where:

$M_{O2}$: Molecular Weight of oxygen gas $M_{N2}$: Molecular Weight of nitrogen gas Therefore, the oxygen concentration P will be obtained through a calculation on the basis of the measurement of mean molecular weight M. When the sample gas is an oxygen-nitrogen mixture, κ=1.4 is reasonable over a wide range of the oxygen-nitrogen mixture ratio.

When the velocity of ultrasonic waves propagating through a sample gas is C(m/sec) and the flow velocity of the sample gas is V(m/sec), the velocity of ultrasonic waves $C_1$(m/sec) propagating in the forward direction relative to the sample gas flow is $C_1 = C+V$, and the velocity of ultrasonic waves $C_2$(m/sec) propagating in the backward direction relative to the sample gas flow is $C_2 = C-V$. Therefore, the velocity of the sample gas flow V(m/sec) is calculated by following equation (3).

$$V = (C_1 - C_2)/2 \quad (3)$$

The flow rate (m³/sec) of the sample gas will be obtained by multiplying the velocity of the sample gas flow by the sectional area (m²) of the conduit through which the sample gas flows.

Methods and apparatuses for measuring the concentration of a certain gas or the flow velocity of a sample gas, by using the above principle, on the basis of the propagation velocity or the propagation time of ultrasonic waves through the sample gas have been developed. For example, Japanese Unexamined Patent Publication (Kokai) No. 6-213877 describes an apparatus for measuring the concentration and the flow rate of a sample gas by measuring the propagation time of ultrasonic waves propagating between two ultrasonic transducers opposingly disposed in a conduit through which the sample gas flows. Further, Japanese Unexamined Patent Publications (Kokai) No. 7-209265 and No. 8-233718 describe an apparatus for measuring the concentration of a certain gas contained in a sample gas by measuring the propagation velocity or propagation time of ultrasonic waves propagating through a volume with a reflecting type apparatus including an ultrasonic transducer and an opposingly disposed reflector.

In such a method and an apparatus for measuring the concentration and the flow rate by using the propagation velocity of the ultrasonic waves, it is necessary to accurately measure the propagation time of the ultrasonic waves. However, the signal generated on the basis of the received ultrasonic waves always includes noise component, which makes difficult to determine the moment when ultrasonic waves are received by the ultrasonic transducer. Therefore, the propagation time of ultrasonic waves is indirectly estimated through a complex signal processing procedure or a complex hardware. For example, Japanese Unexamined Patent Publication (Kokai) No. 9-318644 describes a method for measuring a propagation time of ultrasonic waves in which the waveform of the received ultrasonic waves is integrated. After the results of the integration of the waveform reach a predetermined vale, the first zero-cross time instant is determined as the propagation time of the ultrasonic waves for the measurement of the flow rate. According to the method, the timing of the generation of the zero-cross signal is not fluctuated even if the amplitude of the received waves is fluctuated to some extent. Therefore, the obtained zero-cross time instant is relatively close to the moment when the ultrasonic waves actually reach. However, the obtained zero-cross time instant is not real propagation time of the ultrasonic waves. In particular, when the concentration is measured, the measurement error is strongly affected by the difference between the real propagation time and the zero-cross time instant.

Further, Japanese Unexamined Patent Publication (Kokai) No. 60-138422 describes a flow rate measuring device in which an envelope curve is calculated on the basis of the waveform of the received ultrasonic waves. The rise time of the envelope curve is calculated by an approximate equation to estimate the ultrasonic propagation time. However, a hardware is necessary to sample the received ultrasonic waves and a complex signal processing is necessary to calculate the envelope curve based on the sampled waveform. Therefore, according to the invention of JPP '422, it is difficult to provide a compact device with low cost.

DISCLOSURE OF THE INVENTION

The object of the invention is to provide an ultrasonic apparatus and method for measuring concentration and flow rate of gas, which allow to accurately measure the concentration and flow rate of a sample gas without a complex signal processing and an additional hardware.

According to the present invention, there is provided an ultrasonic apparatus for measuring the concentration and flow rate of a sample gas, comprising:

a conduit for flowing the sample gas;

a first ultrasonic transmission-reception device mounted to the inside of the conduit;

a second ultrasonic transmission-reception device mounted to the inside of the conduit to face the first ultrasonic transmission-reception device;

a transmission-reception switch for switching the operation mode of the first and second ultrasonic transmission-reception devices between a transmission mode for transmitting ultrasonic waves and a reception mode for receiving ultrasonic waves;

a temperature sensor, disposed in the conduit, for measuring the temperature of the sample gas flowing through the conduit;

the first ultrasonic transmission-reception device generating forward ultrasonic waves relative to the flow direction of the sample gas when the device is in the transmission mode and generating backward waveform when the device is in the reception mode on the basis of the received ultrasonic waves generated by the second ultrasonic transmission-reception device;

the second ultrasonic transmission-reception device generating backward ultrasonic waves relative to the flow direction of the sample gas when the device is in the transmission mode and generating forward waveform when the device is in the reception mode on the basis of the received ultrasonic waves generated by the first ultrasonic transmission-reception device;

means for generating trigger signals when the forward and backward waveforms pass over a predetermined level;

means for generating forward and backward zero-cross signals when the forward and backward waveforms pass over a zero level;

propagation time calculation means, coupled to the temperature sensor, the trigger signal generating means and the zero-cross signal generating means, for (1) calculating a possible propagation time range on the basis of the gas temperature detected by the temperature sensor, (2) determining whether or not the phases at which two first trigger signals, respectively generated on the basis of the forward and backward waveforms, coincide with each other, (3) processing the zero-cross signals so that the phases coincide with each other if they do not coincide with each other, (4) obtaining reference zero-cross time instant by calculating mean value of the forward and backward zero-cross time instants, (5) obtaining an ultrasonic reception point by subtracting an integral multiple of the cycle of the ultrasonic waves so that the results of the subtraction falls into the possible propagation time range and (6) estimating the ultrasonic propagation time on the basis of the ultrasonic reception point.

Further, according to another feature of the invention, there is provided a method of measuring the concentration of sample gas flowing through a conduit, comprising the steps of:

generating forward ultrasonic waves relative to the flow direction of the sample gas;

generating backward ultrasonic waves relative to the flow direction of the sample gas;

measuring the temperature of the sample gas flowing through the conduit;

generating trigger signals when the forward and backward waveforms pass over a predetermined level;

generating forward and backward zero-cross signals when the forward and backward waveforms pass over a zero level;

calculating a possible propagation time range on the basis of the gas temperature detected by the temperature sensor;

determining whether or not the phases at which two first trigger signals, respectively generated on the basis of the forward and backward waveforms, coincide with each other;

processing the zero-cross signals so that the phases coincide with each other if they do not coincide with each other;

obtaining reference zero-cross time instant by calculating mean value of the forward and backward zero-cross time instants;

obtaining an ultrasonic reception point by subtracting an integral multiple of the cycle of the ultrasonic waves so that the results of the subtraction falls into the possible propagation time range; and estimating the ultrasonic propagation time on the basis of the ultrasonic reception point.

Further, according to another feature of the invention, there is provided an oxygen concentration system for generating an oxygen enriched gas, comprising an oxygen concentration apparatus for generating an oxygen enriched gas by adsorbing nitrogen to remove the nitrogen from the air; and an ultrasonic apparatus for measuring the concentration of the oxygen in the oxygen enriched gas and flow rate of the oxygen enriched gas, the ultrasonic apparatus comprising:

a conduit for receiving and flowing the oxygen enriched gas;

a first ultrasonic transmission-reception device mounted to the inside of the conduit;

a second ultrasonic transmission-reception device mounted to the inside of the conduit to face the first ultrasonic transmission-reception device;

a transmission-reception switch for switching the operation mode of the first and second ultrasonic transmission-reception devices between a transmission mode for transmitting ultrasonic waves and a reception mode for receiving ultrasonic waves;

a temperature sensor, disposed in the conduit, for measuring the temperature of the oxygen enriched gas flowing through the conduit;

the first ultrasonic transmission-reception device generating forward ultrasonic waves relative to the flow direction of the oxygen enriched gas when the device is in the transmission mode and generating backward waveform when the device is in the reception mode on the basis of the received ultrasonic waves generated by the second ultrasonic transmission-reception device;

the second ultrasonic transmission-reception device generating backward ultrasonic waves relative to the flow direction of the oxygen enriched gas when the device is in the transmission mode and generating forward waveform when the device is in the reception mode on the basis of the received ultrasonic waves generated by the first ultrasonic transmission-reception device;

means for generating trigger signals when the forward and backward waveforms pass over a predetermined level;

means for generating forward and backward zero-cross signals when the forward and backward waveforms pass over a zero level;

propagation time calculation means, coupled to the temperature sensor, the trigger signal generating means and the zero-cross signal generating means, for (1) calculating a possible propagation time range on the basis of the gas temperature detected by the temperature sensor, (2) determining whether or not the phases at which two first trigger signals, respectively generated on the basis of the forward and backward waveforms, coincide with each other, (3) processing the zero-cross signals so that the phases coincide with each other if they do not coincide with each other, (4) obtaining reference zero-cross time instant by calculating mean value of the forward and backward zero-cross time instants, (5) obtaining an ultrasonic reception point by subtracting an integral multiple of the cycle of the ultrasonic waves so that the results of the subtraction falls into the possible propagation time range and (6) estimating the ultrasonic propagation time on the basis of the ultrasonic reception point.

Further, according to another feature of the invention, there is provided an oxygen concentration system for generating an oxygen enriched gas, comprising:

an oxygen concentration apparatus for generating an oxygen enriched gas by adsorbing nitrogen to remove the nitrogen from the air; and an ultrasonic apparatus for measuring the concentration of the oxygen in the oxygen enriched gas and flow rate of the oxygen enriched gas, the ultrasonic apparatus comprising:

a conduit for flowing an objective gas, the concentration of which is to be measured;

a first ultrasonic transmission-reception device mounted to the inside of the conduit;

a second ultrasonic transmission-reception device mounted to the inside of the conduit to face the first ultrasonic transmission-reception device;

the conduit includes a straight potion and perpendicular portions perpendicularly connected to the ends of the straight portion;

the first and second ultrasonic transmission-reception devices are disposed in the perpendicular portions to face the ends of the straight portion; and the distance between the first and second ultrasonic transmission-reception devices and the respective ends of the straight portion of the conduit satisfying the following relation $$0 < D < fxr^2/C$$

where:

D: the distance (m) between the first and second ultrasonic transmission-reception devices and the respective ends of the straight portion f: frequency of the ultrasonic waves in the sample gas (Hz)

r: inner radius of the conduit (m)

C: velocity of the ultrasonic waves (m/sec)

BRIEF DESCRIPTION OF THE DRAWINGS

FIG. 15 shows experimental results of ultrasonic waveforms which were obtained by an apparatus of FIG. 11.

BEST MODE FOR CARRYING OUT THE INVENTION

A preferred embodiment of the present invention will be described below. In the embodiment described below, a sample gas is composed of a mixture of oxygen and nitrogen. However, the measurable sample gas is not limited to a sample gas of oxygen and nitrogen and the present invention can be supplied to a mixture including another gas.

Figure 1:
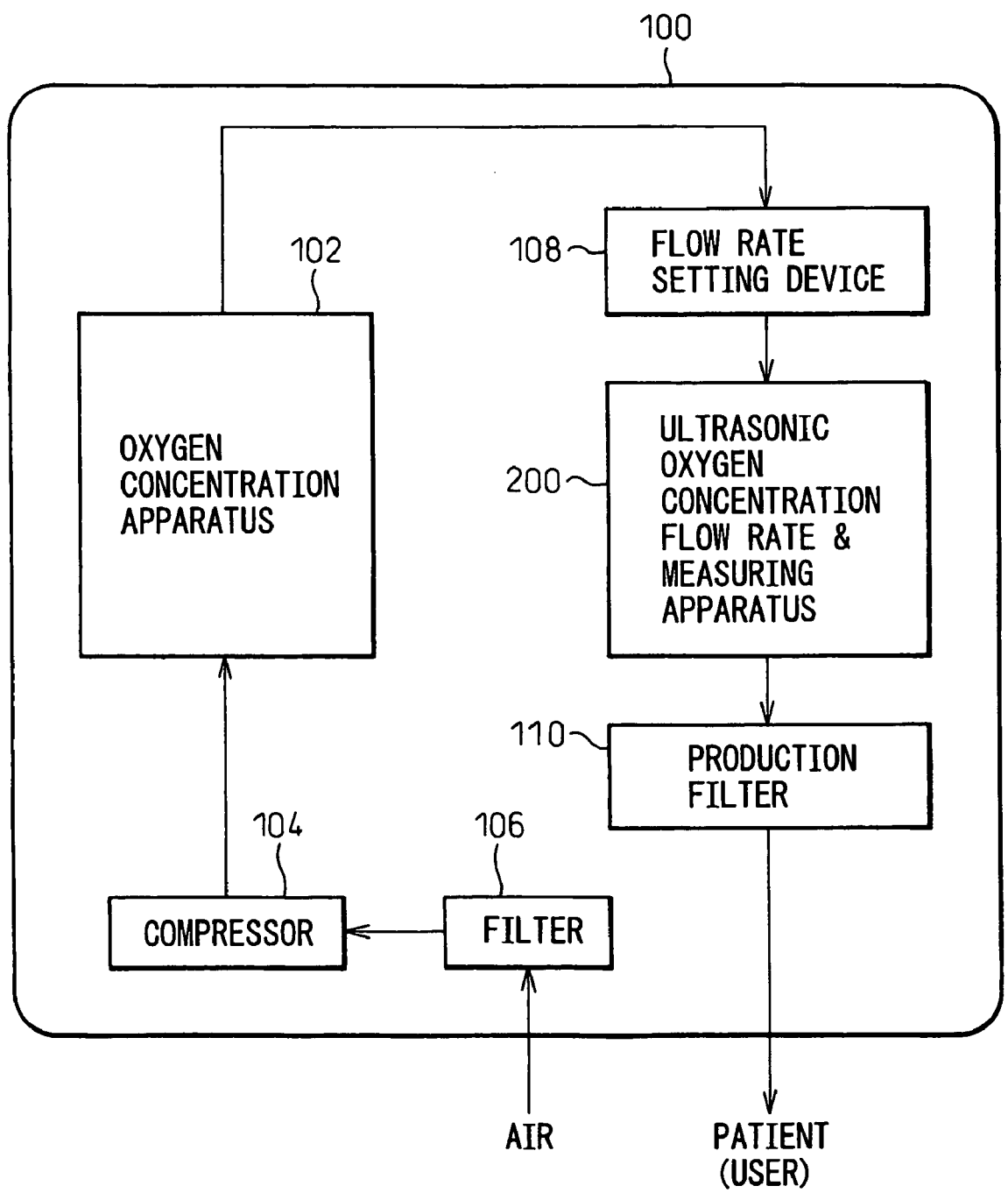
FIG. 1 is a schematic diagram of an oxygen concentration apparatus according the invention.

FIG. 1 shows a schematic diagram of an oxygen concentration system having an ultrasonic gas concentration and flow rate measuring apparatus according to a preferred embodiment of the present invention.

The apparatus 100 includes an oxygen concentration apparatus 102 which produces an oxygen enriched gas by removing nitrogen from the air supplied by a compressor 104 from the outside of the system through a filter 106. The oxygen enriched gas produced by the oxygen concentration apparatus 102 is supplied to an ultrasonic apparatus 200 of the present invention through a flow rate setting device 108, such as a pressure reduction valve. The produced oxygen enriched gas is then supplied to a user or a patient through a production filter 110.

The oxygen concentration apparatus includes a plurality of columns (not shown) for accommodating nitrogen adsorbent such as a zeolite, a piping system (not shown) including conduits for directing the compressed air from the compressor 104 to each of the plurality of columns and for directing the produced oxygen enriched gas from the columns to the flow rate setting device 108 and valves (not shown) disposed in the piping system for selectively opening and closing the conduits so that the adsorbent contained in one of the columns adsorbs nitrogen to produce the oxygen enriched gas and the adsorbent contained in the other columns release the adsorbed nitrogen for the regeneration of the adsorbent.

Figure 2:
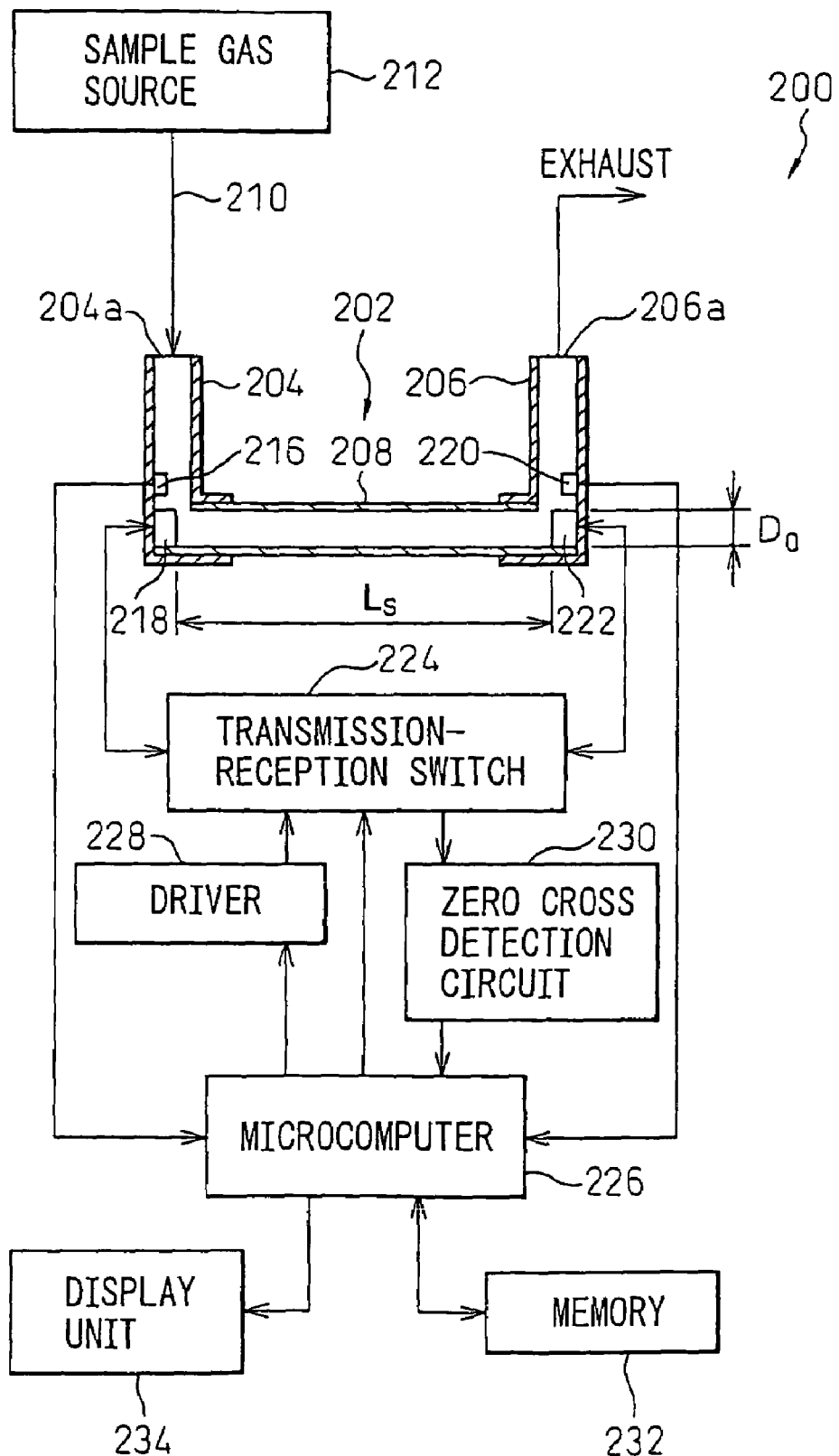
FIG. 2 is a schematic diagram of an ultrasonic apparatus of the invention.

With reference to FIG. 2, the ultrasonic apparatus 200 of the present invention for measuring the concentration and the flow rate of a sample gas will be described below.

The gas concentration and flow rate measuring apparatus 200 includes a conduit 202 for flowing a sample gas or the oxygen enriched gas produced by the oxygen concentration apparatus 102. The conduit 202 has a straight portion 208 and perpendicular portions 204 and 206 connected to the ends of the straight portion. The straight portion 208 comprises a conduit member having a circular section, the diameter of which does not changes along the longitudinal axis. A first ultrasonic transducer 218, providing a first ultrasonic transmission-reception device, is fixedly provided at an end of the inside of the straight portion, and a second ultrasonic transducer 222, providing a second ultrasonic transmission-reception device, is fixedly mounted to the other end of the inside of the straight portion 208 to face the first ultrasonic transducer 218. In this embodiment, the distance between the first and second ultrasonic transducers 218 and 222 is referred to a propagation length $L_s$.

The perpendicular portion 204, disposed at the upstream side relative to the flow direction of the gas through the conduit 202, has an inlet port 204a. The oxygen concentration apparatus 102 is connected to the inlet port 204a as a sample gas source 212 through a supply conduit 210.

The perpendicular portion 206, disposed at the downstream side relative to the flow direction of the gas through the conduit 202, has an outlet port 206a to which the production filter 110 is connected.

A transmission-reception switch 224 is connected to the first and second ultrasonic transducers 218 and 222. The transmission-reception switch 224 independently switches the operation mode of the first and second ultrasonic transducers 218 and 222 between a transmission mode in which the first and second ultrasonic transducers 218 and 222 transmit ultrasonic waves and a reception mode in which the first and second ultrasonic transducers 218 and 222 receive the ultrasonic waves. The transmission-reception switch 224 is connected to a microcomputer 226 so that the switching operation of transmission-reception switch 224 is controlled by the microcomputer 226.

Temperature sensors 216 and 220, for measuring the temperature of the gas flowing through the conduit 202, are disposed preferably in the perpendicular portions 204 and 206 so that they do not disturb the flow in the straight portion 208. The temperature sensors 216 and 220 are connected to the microcomputer 226. In this connection, if the changes in the temperature of the sample gas is small, only one of the temperature sensors 216 or 220 may be disposed.

A driver 228 for driving the first and second ultrasonic transducers 218 and 222, a zero-cross detection circuit 230 for detecting zero-cross time instants of the signals from the first and second ultrasonic transducers 218 and 222, a display unit 234 for indicating, for example, the operating condition of the device 200 and the measurement results and memory 232 including a nonvolatile memory device or a disc device for storing the operation system for the microcomputer 226 and various parameters are connected to the microcomputer 226.

The operation of the ultrasonic concentration and flow rate measuring apparatus 200 of the present embodiment will be described below.

A sample gas, for example an oxygen-nitrogen gas mixture the mixture ratio of which is P:(1−P) (0≦P≦1), is supplied to the conduit 202. At that time, the temperatures of the sample gas are measured by the temperature sensors 216 and 220 and the mean value thereof is stored in the memory 232 as a reference temperature $T_0(K)$. According to the embodiment, the working temperature range of the system 100 is preferably selected, for example 5–35 Celsius degrees.

During the supply of the sample gas, pulses for generating the ultrasonic waves are transmitted to the driver 228 from the microcomputer 226. A pulse voltage is supplied to the first ultrasonic transducer 218 from the driver 228 through the transmission-reception switch 224. The first ultrasonic transducer 218 generates ultrasonic waves corresponding to the pulse voltage. The ultrasonic waves generated by the first ultrasonic transducer 218 propagate through the sample gas flowing through the straight portion 208 of the conduit 202 and are received by the second ultrasonic transducer 222. The second ultrasonic transducer 222 generates an electric signal corresponding to the received ultrasonic waves to the microcomputer 226 through the transmission-reception switch 224 and the zero-cross detection circuit 230. The microcomputer 226 calculates the forward propagation time $t_{s1}$(sec) on the basis of the time when the transmitted pulses are generated to the driver 228 and the time when the electric signal is received from the second ultrasonic transducer 222.

Then, the transmission-reception switch 224 switches the operation mode of the first ultrasonic transducer 218 from the transmission mode to the reception mode right after the electric signal from the second ultrasonic transducer 222 is received and also switches the operation mode of the second ultrasonic transducer 222 from the reception mode to the transmission mode. Thereafter, pulses for generating the ultrasonic waves are transmitted to the driver 228 from the microcomputer 226. A pulse voltage is supplied to the second ultrasonic transducer 222 from the driver 228 through the transmission-reception switch 224. The second ultrasonic transducer 222 generates ultrasonic waves corresponding to the pulse voltage. The ultrasonic waves are received by the first ultrasonic transducer 218. The first ultrasonic transducer 218 generates an electric signal corresponding to the received ultrasonic waves to the microcomputer 226 through the transmission-reception switch 224 and the zero-cross detection circuit 230. The microcomputer 226 calculates the backward propagation time $t_{s2}$(sec) on the basis of the time when the transmitted pulses are generated to the driver 228 and the time when the electric signal is received from the first ultrasonic transducer 218.

By obtaining the mean value of $t_{s1}$ and $t_{s2}$, the affection of the flow of the sample gas in the conduit 202 can be removed. The ultrasonic propagation time $t_s$ in the stationary sample gas is defined by following equation (4).

$$t_s = (t_{s1} + t_{s2})/2 \tag{4}$$

The microcomputer 226 then calculates the ultrasonic propagation velocity $C_s$(m/sec) through the stationary sample gas by flowing equation (5).

$$C_S = L_S/t_S \tag{5}$$

The concentration of oxygen $P_S$ is obtained by following equation (6) on the basis of equations (1) and (2).

$$P_S = (\kappa R T_S/C_S^2 - M_{N2})/(M_{O2} - M_{N2}) \tag{6}$$

Further, the concentration of oxygen in the sample can be obtained as a ratio of the ultrasonic propagation velocity in the sample gas and the ultrasonic propagation velocities in 100% of oxygen gas and 100% of nitrogen gas. That is, the ultrasonic propagation velocity $C_{O2}$(m/sec) at temperature $T_S(K)$ through 100% of oxygen gas and the ultrasonic propagation velocity $C_{N2}$(m/sec) at temperature $T_S(K)$ through 100% of nitrogen gas can be easily obtained by using equation (1). Thus, $P_S$ can be calculated by following equation (7) with the ultrasonic propagation velocity $C_S$(m/sec) through the sample gas.

$$P_S = (1/C_S^2 - 1/C_{N2}^2)/(1/C_{O2}^2 - 1/C_{N2}^2) \tag{7}$$

Such calculations are conducted by the microcomputer 226, and the results are indicated by the display unit 234.

Next, the explanation will be directed to a method of obtaining $t_{s1}$ and $t_{s2}$. In this connection, the moment when the first or second ultrasonic transducer 218 or 222 transmits the ultrasonic waves is referred to as an emission time and the moment when the first or second ultrasonic transducer 218 or 222 receives the ultrasonic waves is referred to as an ultrasonic reception point in the present application.

Figure 3A:
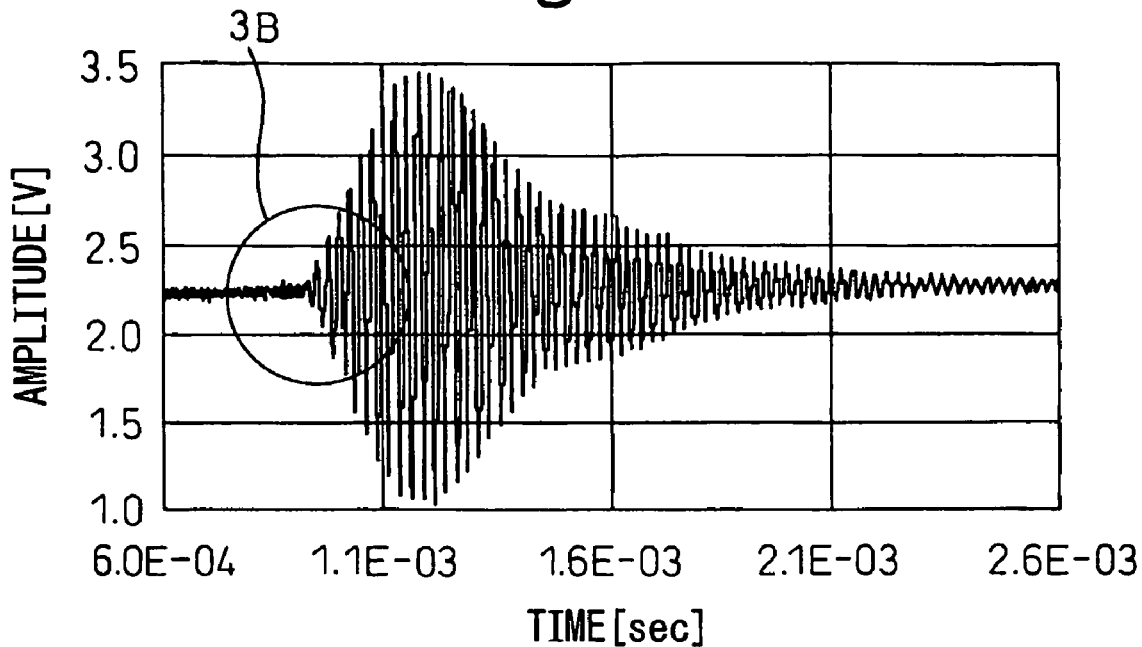
FIG. 3A is a waveform based on the received ultrasonic waves.
Figure 3B:
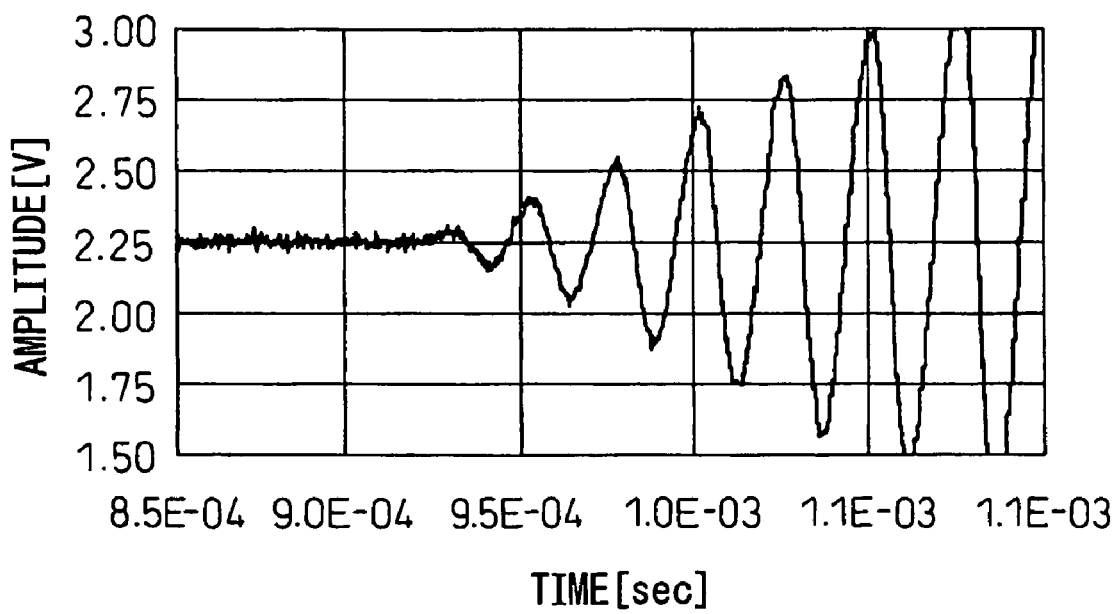
FIG. 3B is an enlarged illustration of a portion of the waveform shown in FIG. 3A.

FIG. 3A shows a typical ultrasonic waveform received by the microcomputer 226 and FIG. 3B is an enlargement of a portion of the waveform shown by circle 3B. As shown by FIGS. 3A and 3B, the waveform includes a various noise components which make difficult to detect the ultrasonic reception point of the ultrasonic waves propagating through the sample gas. Therefore, according to the present invention, the ultrasonic reception point is estimated on basis of the zero-cross time instant of the waveform which is detected after the amplitude of the waveform sufficiently increases to an extent. For this purpose, the zero-cross detection circuit 230 includes a zero-cross comparator and a trigger comparator.

Figure 4:
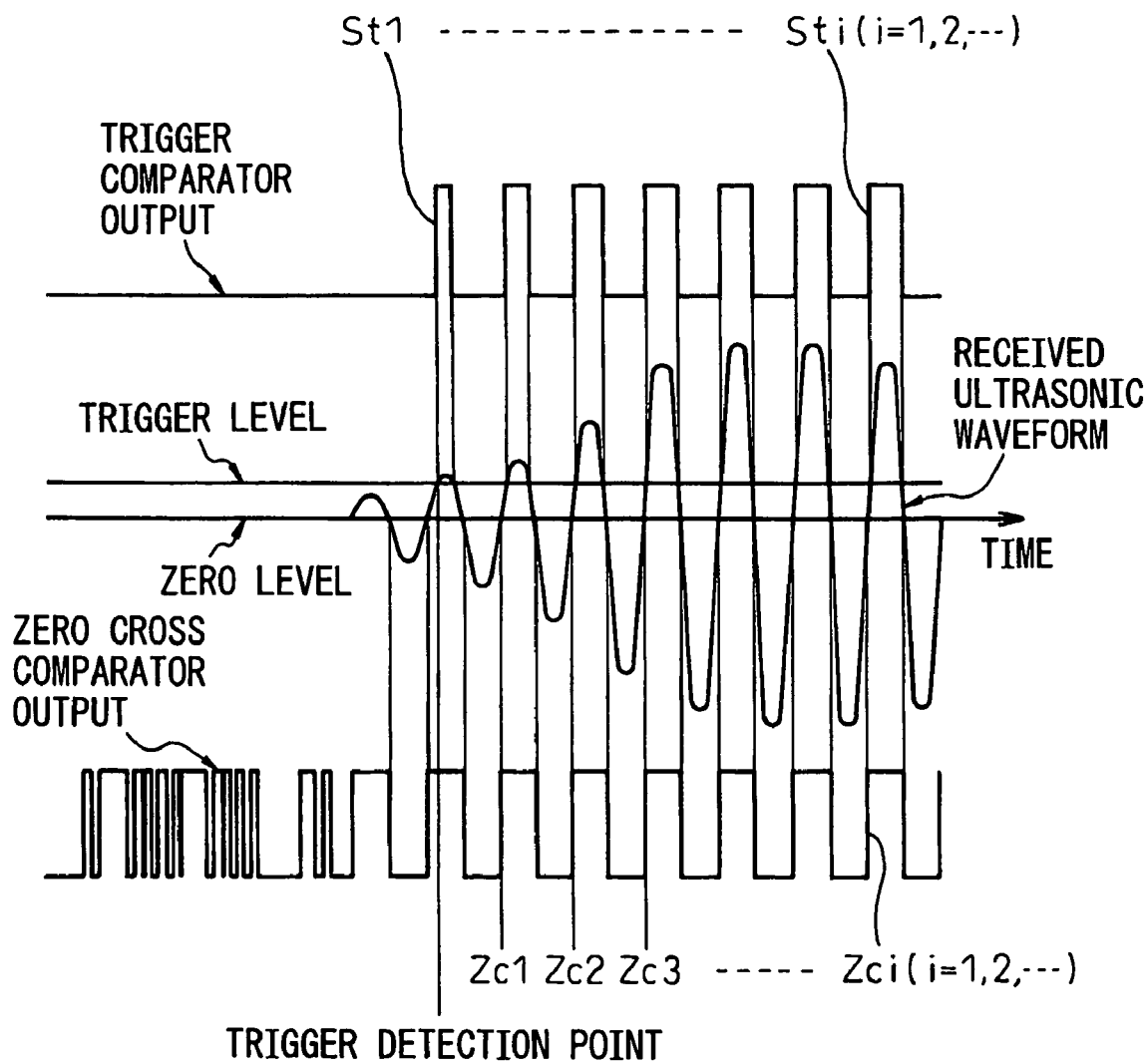
FIG. 4 is an illustration showing the ultrasonic waveform with the trigger signals and the zero-cross signals.

Referring to FIG. 4, the trigger comparator outputs a trigger signals $S_{tr}$ to the microcomputer 226 when the waveform upwardly passes over a predetermined level. The zero-cross comparator outputs a zero-cross signal $Z_{ci}$ to the microcomputer 226 when the waveform upwardly passes over the zero level. The microcomputer 226 determines each of the zero-cross signals $Z_{ci}$ as a zero-cross time instant after the first trigger signal $S_{t1}$, is received by the microcomputer 226. Preferably, the microcomputer 226 determines first three zero-cross signals as first to third zero-cross time instants $Z_{c1}$, $Z_{c2}$ and $Z_{c3}$.

The interval between each of the zero-cross time instants theoretically corresponds to the cycle of the ultrasonic waves. Therefore, the ultrasonic reception point can be estimated by tracing back from the first zero-cross time instant $Z_{c1}$ along the time axis by an integral multiple of the cycle of the ultrasonic waves and therefore, the propagation time can be estimated by subtracting the emission time and an integral multiple of the cycle of the ultrasonic waves from the ultrasonic reception point.

Figure 5:
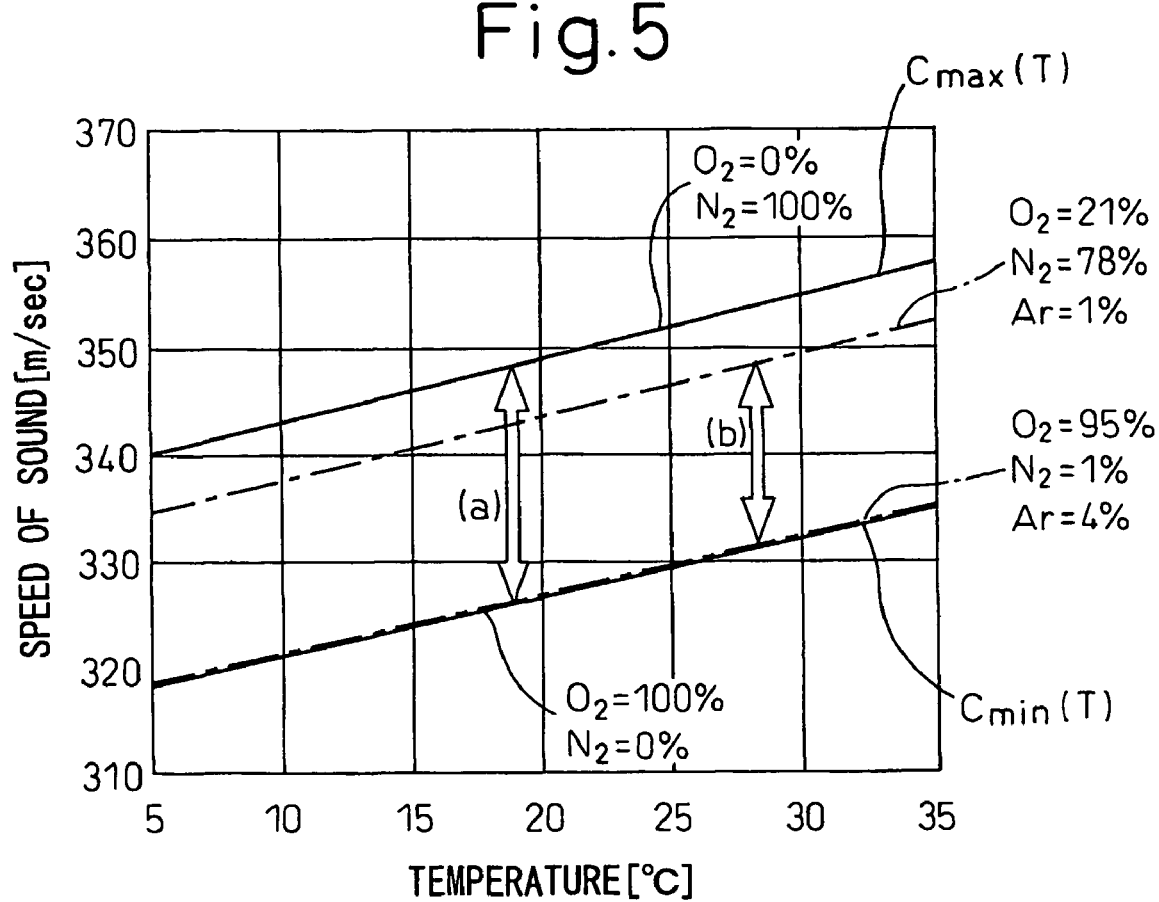
FIG. 5 is a graph showing the relation between the velocity of the ultrasonic waves and the temperature.

As described above, the velocity of ultrasonic waves C(m/sec) propagating through a stationary gas is presented by equation (1). For example, the velocity of ultrasonic waves through a pure nitrogen gas at 20 Celsius degrees is 349.1 m/sec, and the velocity of ultrasonic waves through a pure oxygen gas at 20 Celsius degrees is 326.6 m/sec. Therefore, at 20 Celsius degrees, the velocity of ultrasonic waves through an oxygen-nitrogen gas mixture falls within the rage of 326.6 to 49.1 m/sec. FIG. 5 is a graph showing the relation between the velocity of ultrasonic waves and the gas temperature, in which the upper and lower limits of the ultrasonic velocity through an oxygen-nitrogen gas mixture are indicated by $C_{max}(T)$ and $C_{min}(T)$. The possible propagation time rage is $L_s/C_{max}(T)$ to $L_s/C_{min}(T)$. Therefore, if the propagation length $L_s$ is selected to satisfy following relation (8), only one integer can be selected which allows the ultrasonic reception point to fall within the possible propagation time range.

$$(L_s/C_{min}(T)-L_s/C_{max}(T))<1/f \quad (8)$$

where:

f: frequency of the ultrasonic waves in the sample gas

The gas temperature T which gives the maximum value of $(L_s/C_{max}(T)-L_s/C_{min}(T))$ is the lower limit of the working temperature. If the working temperature is 5 Celsius degrees, and the frequency of the ultrasonic waves is 40 KHz, the propagation length $L_s$ which satisfies relation (8) is calculated as follows.

$$L_s<12.3 \text{ cm} \quad (9)$$

According to the embodiment, $L_s=0.1$ m is employed as an example.

Figure 6:
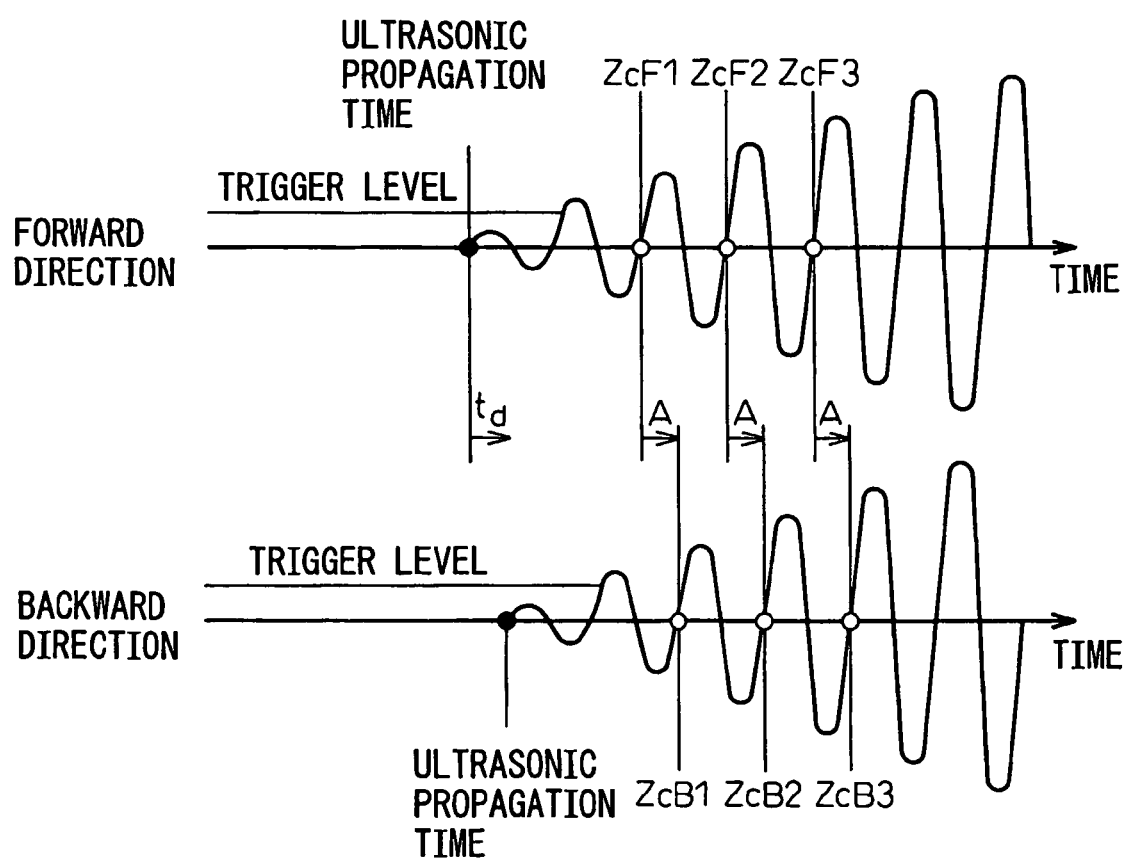
FIG. 6 is an illustration showing forward and backward ultrasonic waveforms in case that the phases, at which the trigger signals are generated, coincide with each other.

In order to obtain the ultrasonic propagation time $t_s$, the forward and backward propagation times $t_{s1}$ and $t_{s2}$ is previously measured. With reference to FIG. 6, the trigger signals are generated when the second waves in both the forward and backward waveforms passes over the trigger level. In this case, the trigger signals are generated at the same timing or phase relative to the waveforms and the difference in the zero-cross time instants between the forward and backward waves, $A=Z_{cBi}-Z_{cFi}$, is substantially equal to the difference $t_d$ in propagation times $t_{s1}$ and $t_{s2}$ between the forward and backward waves ($Z_{cFi}$: the zero-cross time instants of the forward waveform, $Z_{cBi}$: the zero-cross time instants of the backward waveform, i=1, 2, 3 ... (wave number)).

Figure 7:
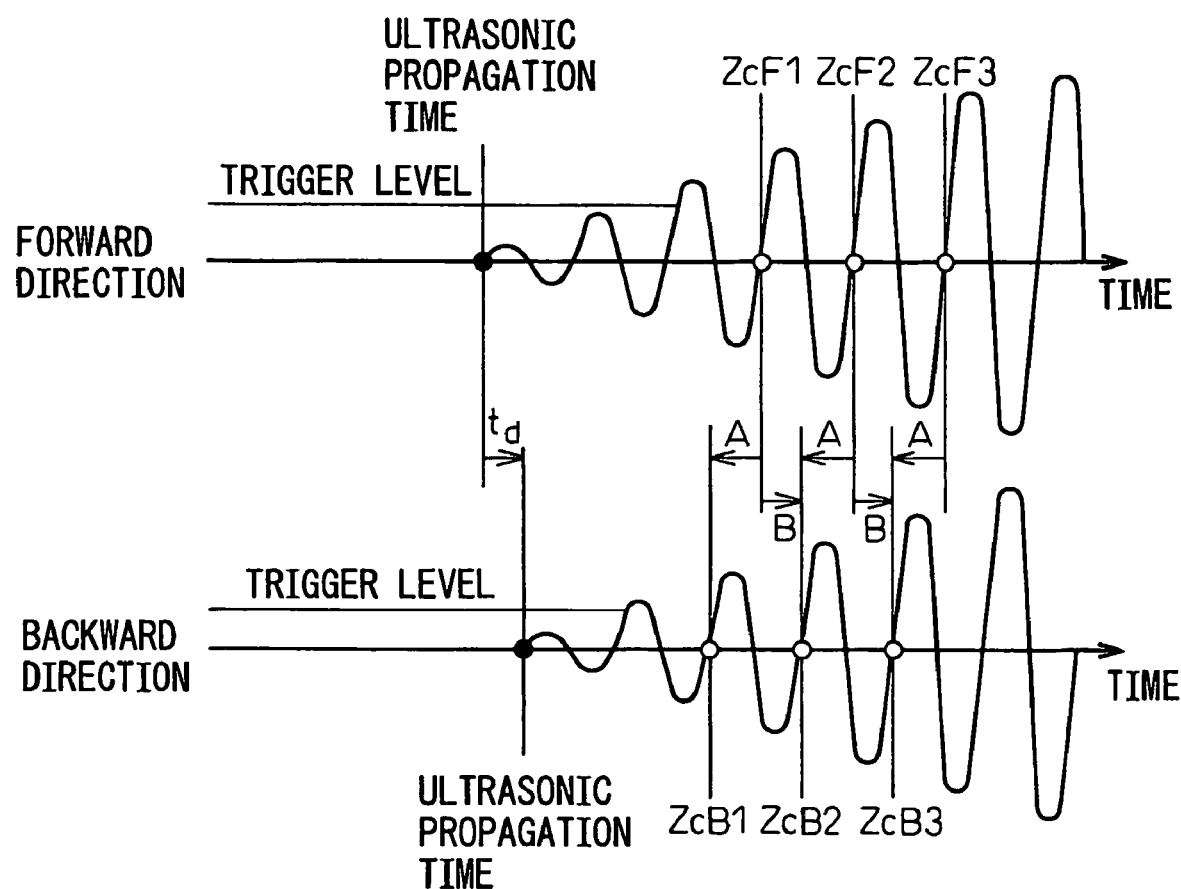
FIG. 7 is an illustration similar to that of FIG. 6 in case that the phases do not coincide with each other.

However, the trigger signals $S_{ti}$ are often generated at different phases of the waveforms between the forward and backward waves, even if the same trigger level is used. Referring to FIG. 7, for the forward waves, the trigger signal is generated when the third wave passes over the trigger level and for the backward waves, the trigger signal is generated when the second wave passes over the trigger level. Therefore, the trigger signal for the backward waves is generated at one cycle earlier than the trigger signal for the forward waves. In this case, the difference in the zero-cross time instants between the forward and backward waves, $A=Z_{cBi}-Z_{cFi}$, gives a negative value. If the sample gas flows through the conduit 202, $A=Z_{cBi}-Z_{cFi}$ must not become negative. Therefore, if $A=Z_{cBi}-Z_{cFi}$ gives a negative value, it is apparent that the trigger signal for the backward waves is generated earlier than the trigger signal for the forward waves.

Figure 8:
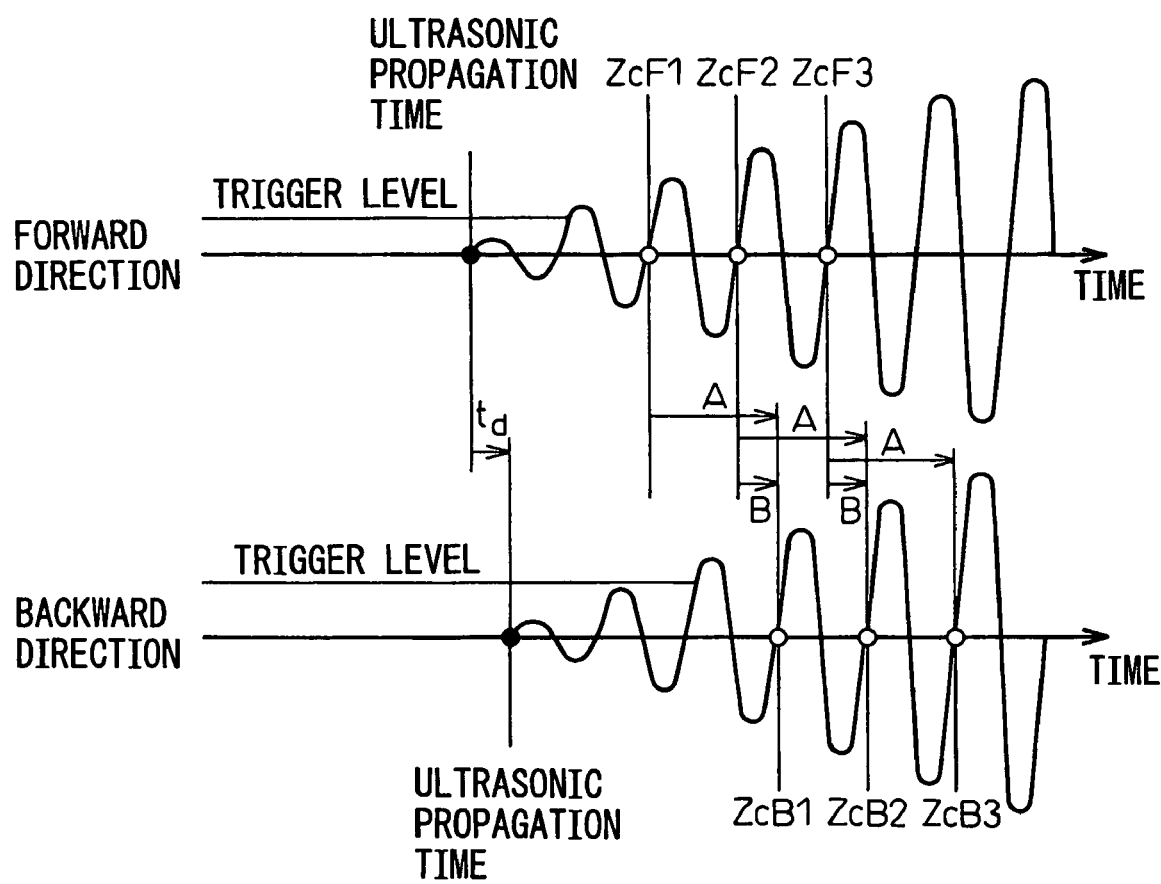
FIG. 8 is an illustration similar to that of FIG. 6 in case that the phases do not coincide with each other.

On the other hand, referring to FIG. 8, for the forward waves, the trigger signal is generated when the second wave passes over the trigger level and for the backward waves, the trigger signal is generated when the third wave passes over the trigger level. In this case, the difference in the zero-cross time instants between the forward and backward waves, $A=Z_{cBi}-Z_{cFi}$, exceeds one cycle of the ultrasonic waves, which indicates that the trigger signal for the forward waves is generated earlier than the trigger signal for the backward waves.

According to the embodiment of the invention, the conduit 202 is designed so that the propagation time difference $t_d$ between the forward and backward waves always falls within one cycle of the ultrasonic waves. This feature allows the microcomputer 226 to distinguish the cases shown in FIGS. 7 and 8 from each other and to calculate the propagation time difference $t_d$. That is, if $A=Z_{cBi}-Z_{cFi}$ is negative, the case is as shown in FIG. 7 and if $A=Z_{cBi}-Z_{cFi}$ exceeds one cycle of the ultrasonic waves the case is as shown in FIG. 8.

Thus, the configuration of conduit 202 which has the above feature will be described below.

The possible range of the flow velocity V (m/sec) of the sample gas is presented by following inequality (10).

$$0 \leq V \leq Q/(60000\pi r^2) \quad (10)$$

where:

Q: flow rate of the sample gas (litter/min)

r: inner radius of the conduit (m)

As described above, the velocity of ultrasonic waves propagated in the forward direction relative to the sample gas flow is $C_1=C+V$, and the velocity of ultrasonic waves propagated in the backward direction relative to the sample gas flow is $C_2=C-V$.

Where:

C: the velocity of ultrasonic waves propagating through a stationary sample gas (m/sec)

$C_1$: the velocity of the ultrasonic waves propagated in the forward direction relative to the sample gas flow (m/sec)

$C_2$: the velocity of ultrasonic waves propagated in the backward direction relative to the sample gas flow (m/sec)

V: the flow velocity (m/sec)

The propagation time difference $t_d$ is calculated by the following equation.

$$\begin{aligned} t_d &= L_s/C_2 - L_s/C_1 \\ &= L_s/(C-V) - L_s/(C+V) \end{aligned} \quad (11)$$

Therefore, if the inner radius of the conduit 202 satisfies following relation (12), the propagation time difference $t_d$ becomes smaller than the cycle of the ultrasonic waves.

$$L_s/(C-Q/(60000\pi r^2))-L_s/(C+Q/(60000\pi r^2))<1/f \quad (12)$$

The left term of inequality (12) is maximized when the velocity of the ultrasonic waves through the conduit 202 is minimum (C=$C_{min}$(5 Celsius degrees)=318.1 m/sec). Therefore, for example, if the frequency of the ultrasonic waves through the conduit 202 is 40 (KHz), the flow rate Q=10 (litter/min) and the length of the conduit 202 is 10 (cm), then the inner radius r (mm) of the conduit 202 is r>2.05 (mm). According to the embodiment, r=2.5 (mm) is selected as an example.

Next. the method for measuring the concentration and flow rate of a sample gas will be described in detail below.

First, in case shown in FIG. 6, the propagation time difference $t_d$ between the forward and backward waves is obtained by A=$Z_{cBi}-Z_{cFi}$, because, as described above, the propagation time difference $t_d$ is substantially equal to the difference A=$Z_{cBi}-Z_{cFi}$. In case shown in FIG. 7, the propagation time difference $t_d$ is obtained by B=$Z_{cBi+1}-Z_{cFi}$. Further, in case shown in FIG. 8, the propagation time difference $t_d$ is obtained by B=$Z_{cBi}-Z_{cFi+1}$. Preferably, a plurality of the values A or B are obtained for arithmetic average.

Next, the velocity of the ultrasonic waves through the sample gas is estimated with the assumption that the sample gas is in stationary state. For this purpose, the phase difference in the outputs of the trigger signals is previously determined on the basis of the value of A. If there is no phase difference, as shown in FIG. 6, mean value $Z_{c\_ave}$ of first zero-cross time instants of the forward and backward waveforms is calculated by the following equation.

$$Z_{c\_ave}=(Z_{cF1}+Z_{cB1})/2 \quad (13)$$

In case shown in FIG. 7, mean value $Z_{c\_ave}$ of first zero-cross time instants of the forward and backward waveforms is calculated by the following equation.

$$Z_{c\_ave}=(Z_{cF1}+Z_{cB2})/2 \quad (14)$$

In case shown in FIG. 8, mean value $Z_{c\_ave}$ of first zero-cross time instants of the forward and backward waveforms is calculated by the following equation.

$$Z_{c\_ave}=(Z_{cF2}+Z_{cB1})/2 \quad (15)$$

The mean value $Z_{c\_ave}$ can be considered as the first zero-cross time instant which is obtained with the assumption of the ultrasonic waves through the stationary sample gas. $Z_{c\_ave}$ is referred to a reference zero-cross time instant in the present application.

Figure 9:
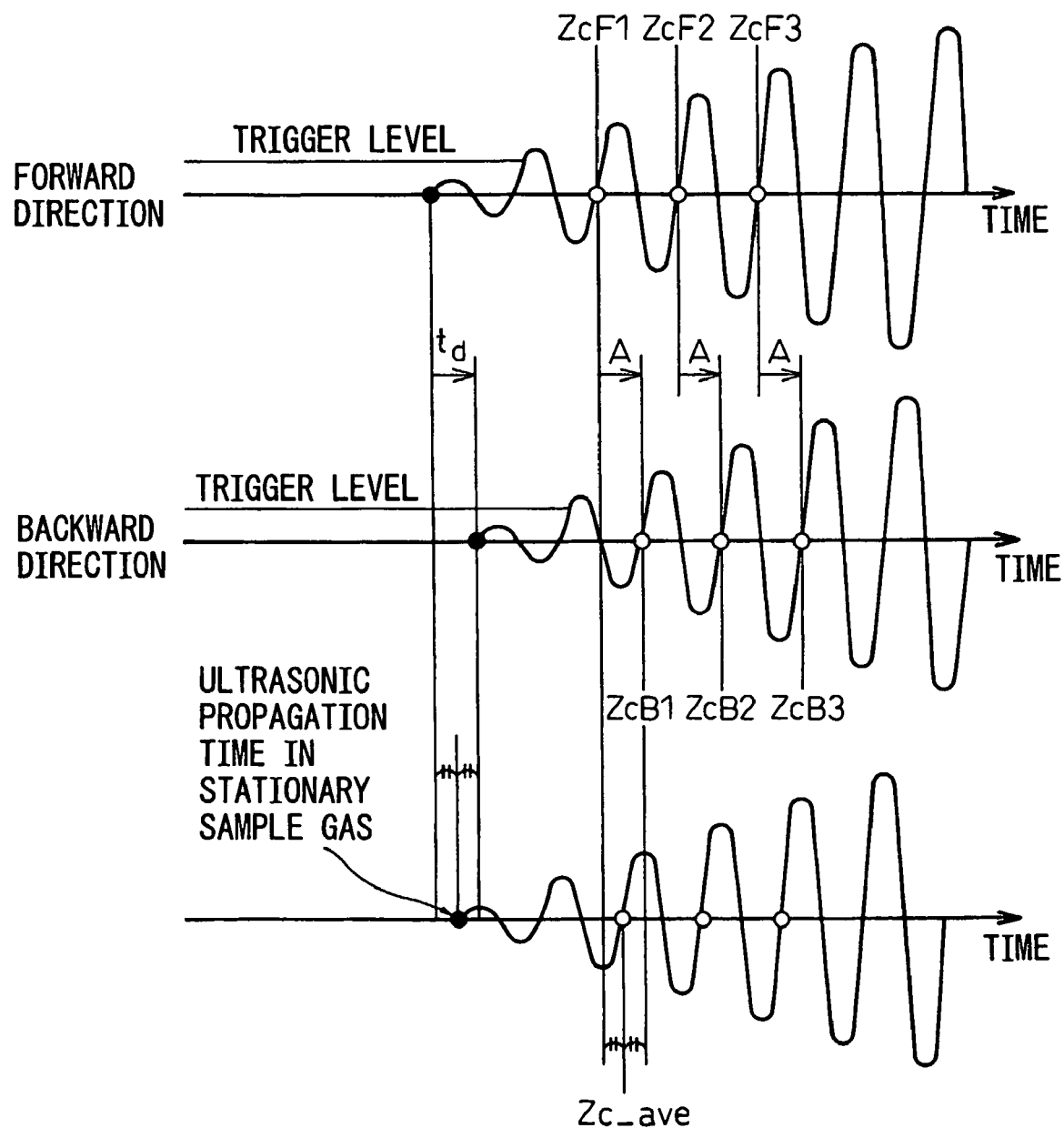
FIG. 9 is an explanatory illustration for explaining the way for obtaining the zero-cross time instant with an assumption that the sample gas is in stationary state.
Figure 10:
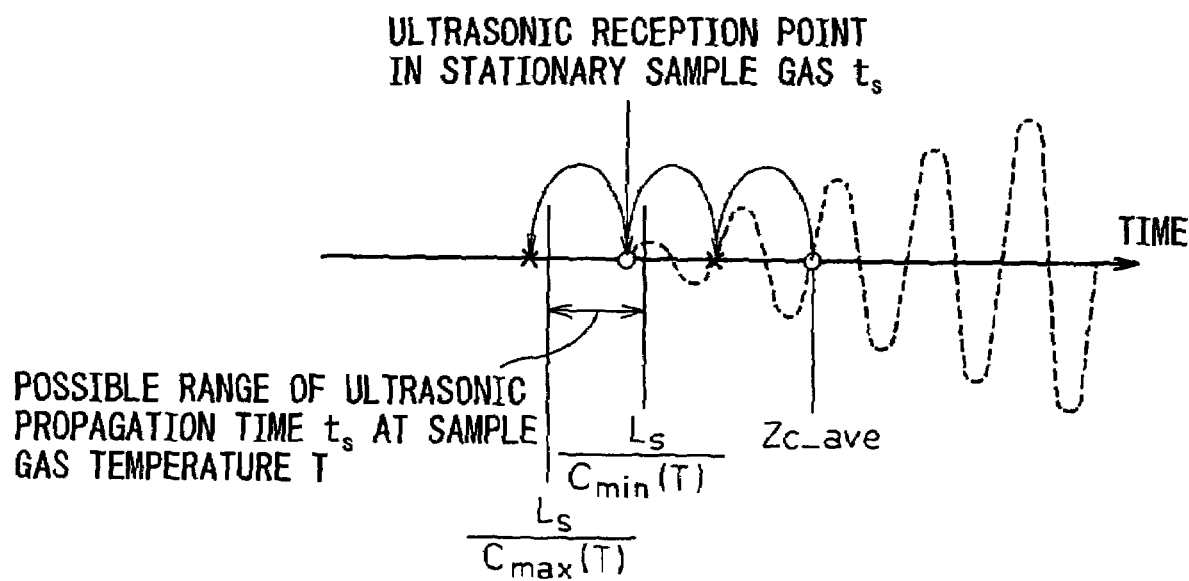
FIG. 10 is an explanatory illustration for explaining the way for obtaining the ultrasonic reception point.

As described above, the length of the conduit 102 is designed so that only one integer is selected allowing the ultrasonic reception point to fall in the possible range of the propagation time (FIG. 9). Therefore, the ultrasonic propagation time $t_s$ is estimated by tracing back from the first zero-cross time instant $Z_{c\_ave}$ along the time axis by an integral multiple of the cycle of the ultrasonic waves until the ultrasonic reception point falls in the possible range.

The velocity of the ultrasonic waves Cs through the stationary sample gas is estimated by following equation (16).

$$C_s=L_s/t_s \quad (16)$$

The concentration of oxygen $P_s$ is obtained by equation (6) or (7) with the calculated $C_s$.

The forward and backward propagation times $t_{s1}$ and $t_{s2}$ through the sample gas flowing through the conduit 202 are estimated by following equations (17) and (18).

$$t_{s1}=t_s-t_d/2 \quad (17)$$

$$t_{s1}=t_s+t_d/2 \quad (18)$$

The forward and backward velocities $C_1$ and $C_2$ of the ultrasonic waves through the sample gas flowing through the conduit 202 are estimated by following equations (19) and (20).

$$C_1=L_s/t_{s1} \quad (19)$$

$$C_2=L_s/t_{s2} \quad (20)$$

Then, the flow velocity V of the sample gas through the conduit 202 is obtained by equations (3), (19) and (20). Further, the flow rate Q of the sample gas is calculated by following equation (21).

$$Q=6000\pi r^2 V \quad (21)$$

Next, with reference to FIGS. 11 to 15, a preferred embodiment of the ultrasonic concentration and flow rate measurement apparatus will be described below.

The ultrasonic concentration and flow rate measurement apparatus 10 includes a conduit 27 which provides the conduit 202 of the embodiment of FIG. 2. Housings 25 and 26, for enclosing first and second ultrasonic transducers 20 and 21, secured to the ends of the conduit 27 by welded portions 41 and 42. The housings 25 and 26 include ports 28 and 29 extending perpendicular to the conduit 27 to provide the inlet and outlet portions 204a and 206a of the embodiment of FIG. 2. The conduit 27 and the housings 25 and 26 are preferably made of the same metallic material such as an aluminum alloy.

The conduit 27 and the housings 25 and 26 are secured at one point to a substrate 30 or a housing of the oxygen concentration apparatus by a screw 45. This configuration allows the longitudinal deformation of the conduit 27 freely from external force which may be generated when the conduit 27 is thermally deformed.

Covers 23 and 24 are attached to the housings 25 and 26 to close the end openings of the housings by screws 43 and 44 with O-rings 39 and 40 being clamped between the housings 25 and 26 and the covers 23 and 24. The first and second ultrasonic transducers 20 and 21 are attached to the inner surfaces of the covers 23 and 24. The first and second ultrasonic transducers 20 and 21 generate 40 KHz of ultrasonic waves.

Further, temperature sensors 37 and 38 for detecting the gas temperature are attached to the inner surfaces of the covers 23 and 24. The first and second ultrasonic transducers 20 and 21 and the temperature sensors 37 and 38 are coupled to the microcomputer 226 through connectors 31 and 34 attached to the outer surfaces of the covers 23 and, 24, cables 33 and 36 and connectors 32 and 35 mounted on the substrate 30.

Figure 12:
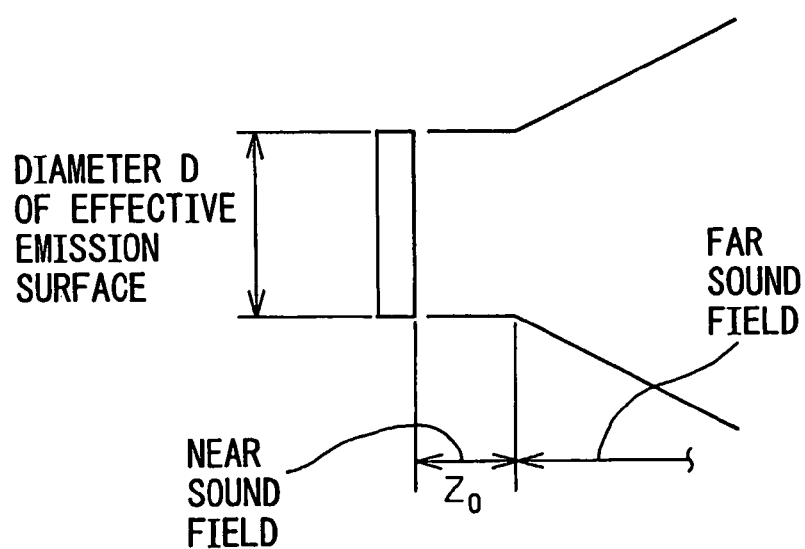
FIG. 12 is an explanatory illustration for explaining the sound field formed at the front of an ultrasonic transducer.

Distance D between the end faces of the first and second ultrasonic transducers 20 and 21 and the respective ends of the conduit 27 is a significant design matter. Generally, the sound field formed by the ultrasonic waves from an ultrasonic transducer includes near and far sound fields, as shown in FIG. 12. The ultrasonic waves propagate linearly through the near sound field and on the other hand, in the far sound field, spread in the form of spherical waves. Therefore, if the ends of the conduit 27 are out of the near sound field, the ultrasonic energy transmitted in the conduit 27 is reduced compared with conduit having the ends disposed in the near sound field and therefore, the sound/noise ratio of the signal from the transducers is reduced.

It is known that the boundary between the near and far sound fields is presented at a point $Z_0$ the distance D of which from the end face of an ultrasonic transducer along the center line of the transducer is defined by following equation (22).

$$D=fxr^2/C \quad (22)$$

Where:

f: frequency of the ultrasonic waves in the sample gas (Hz)

r: inner radius of the conduit (m)

C: velocity of the ultrasonic waves (m/sec)

As described above, the velocity C through a sample gas is defined by equation (1). Therefore, the higher the gas temperature and the smaller the molecular weight, the higher the velocity C becomes. According the embodiment, the condition which maximizes $Z_0$ is that, for example, the sample gas is the air at 35 Celsius degrees and then, $Z_0$ is about 1.4 mm.

Figure 11:
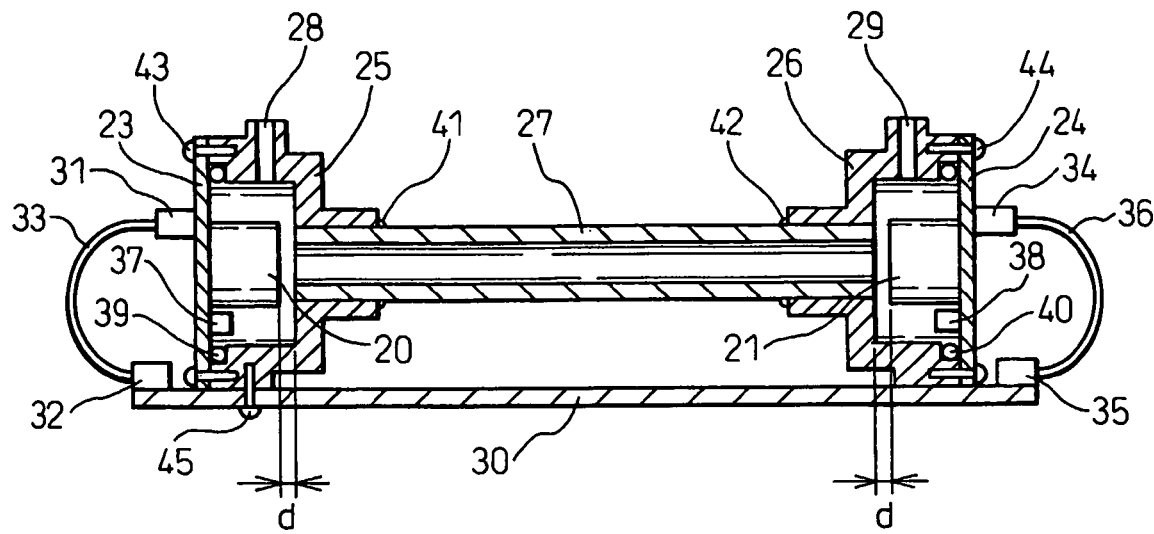
FIG. 11 is a section of the ultrasonic apparatus according to another embodiment of the invention.
Figure 13:
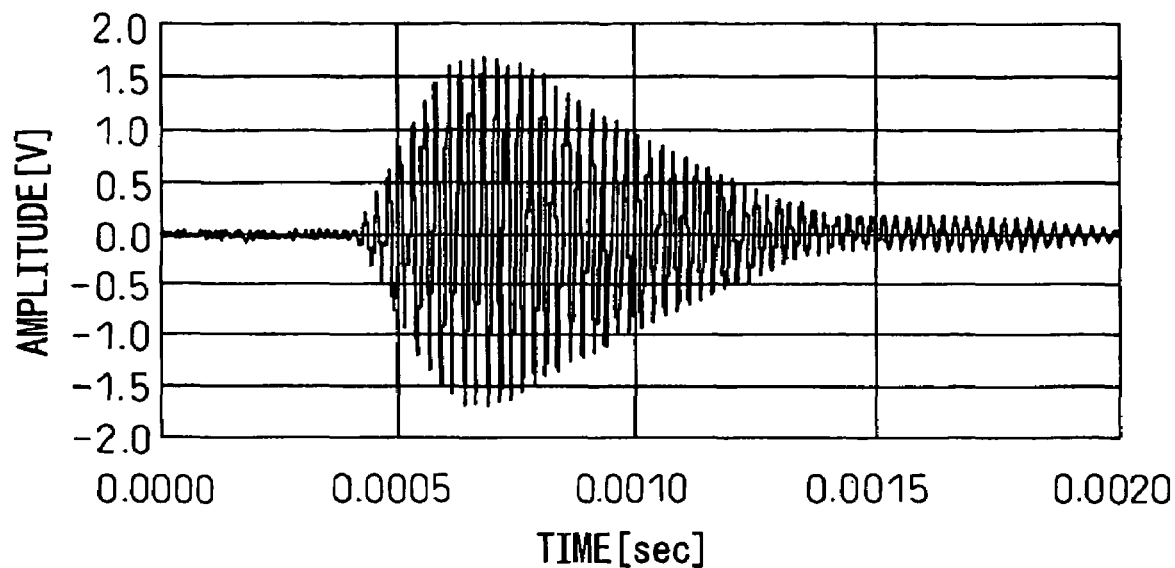
FIG. 13 shows experimental results of ultrasonic waveforms which were obtained by an apparatus of FIG. 11.
Figure 14:
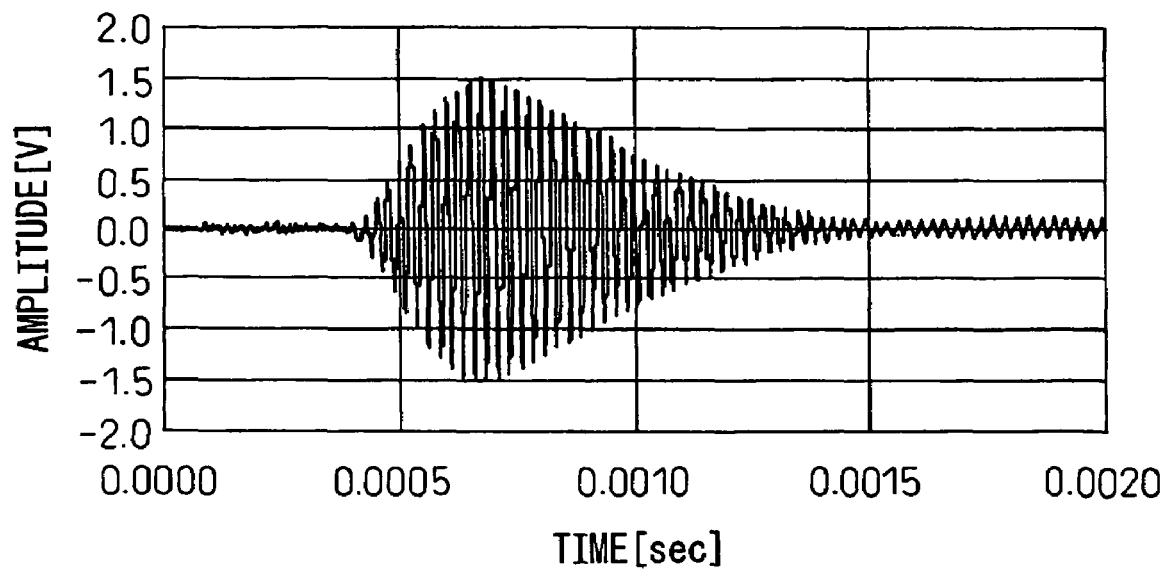
FIG. 14 shows experimental results of ultrasonic waveforms which were obtained by an apparatus of FIG. 11.

FIGS. 13–15 show experimental results of ultrasonic waveforms which were obtained by an apparatus of FIG. 11 with the distance d of 0.3 mm, 1.0 mm and 1.8 mm. The experimental results suggest that the ultrasonic energy received by the ultrasonic transducer is significantly reduced when the distance d is 1.8 mm compared with the cases of the distance d of 0.3 mm and 1.0 mm.

The invention claimed is:

1. An ultrasonic apparatus for measuring the concentration and flow rate of a sample gas, comprising:
a conduit for flowing the sample gas;
a first ultrasonic transmission-reception device mounted to the inside of the conduit;
a second ultrasonic transmission-reception device mounted to the inside of the conduit to face the first ultrasonic transmission-reception device;
a transmission-reception switch for switching the operation mode of the first and second ultrasonic transmission-reception devices between a transmission mode for transmitting ultrasonic waves and a reception mode for receiving ultrasonic waves;
a temperature sensor, disposed in the conduit, for measuring the temperature of the sample gas flowing through the conduit;
the first ultrasonic transmission-reception device generating forward ultrasonic waves relative to the flow direction of the sample gas when the device is in the transmission mode and generating backward waveform when the device is in the reception mode on the basis of the received ultrasonic waves generated by the second ultrasonic transmission-reception device;
the second ultrasonic transmission-reception device generating backward ultrasonic waves relative to the flow direction of the sample gas when the device is in the transmission mode and generating forward waveform when the device is in the reception mode on the basis of the received ultrasonic waves generated by the first ultrasonic transmission-reception device;
means for generating trigger signals when the forward and backward waveforms pass over a predetermined level;
means for generating forward and backward zero-cross signals when the forward and backward waveforms pass over a zero level;
propagation time calculation means, coupled to the temperature sensor, the trigger signal generating means and the zero-cross signal generating means, for (1) calculating a possible propagation time range on the basis of the gas temperature detected by the temperature sensor, (2) determining whether or not the phases at which two first trigger signals, respectively generated on the basis of the forward and backward waveforms, coincide with each other, (3) processing the zero-cross signals so that the phases coincide with each other if they do not coincide with each other, (4) obtaining reference zero-cross time instant by calculating mean value of the forward and backward zero-cross time instants, (5) obtaining an ultrasonic reception point by subtracting an integral multiple of the cycle of the ultrasonic waves so that the results of the subtraction falls into the possible propagation time range and (6) estimating the ultrasonic propagation time on the basis of the ultrasonic reception point.

2. An ultrasonic apparatus according to claim 1 wherein the distance along the conduit between first and second ultrasonic transmission-reception devices is selected so that only one result of the subtraction falls into the possible propagation time range determined over possible working conditions of the ultrasonic apparatus.

3. An ultrasonic apparatus according to claim 2 wherein the distance along the conduit between first and second ultrasonic transmission-reception devices is sleeted to satisfy the following relation $$(L_s/C_{min}(T_{min})-L_s/C_{max}(T_{min}))<1/f$$

where:
$L_s$: propagation length (m)
f: frequency of the ultrasonic waves in the sample gas
$C_{min}(T_{min})$: the lower limit of the ultrasonic velocity (m/sec) through the sample gas at the lowest working temperature $T_{min}$ (Celsius degrees)
$C_{max}(T_{min})$: the upper limit of the ultrasonic velocity (m/sec) through the sample gas at the lowest working temperature $T_{min}$ (Celsius degrees).

4. An ultrasonic apparatus according to claim 1 wherein the inner radius of the conduit is selected so that the difference between the forward and backward propagation time is smaller than the cycle of the ultrasonic waves under the working condition of the sample gas.

5. An ultrasonic apparatus according to claim 1 wherein the inner radius of the conduit is selected to satisfy the following relation $$L_s/(C_{min}(T_{min})-Q_{max}/(60000\pi r^2))$$
$$-L_s/(C_{min}(T_{min})+Q_{max}/(60000\pi r^2))<1/f$$

where:
$L_s$: propagation length (m)
R: inner radius of the conduit (m)
f: frequency of the ultrasonic waves in the sample gas
$C_{min}(T_{min})$: the lower limit of the ultrasonic velocity (m/sec) through the sample gas at the lowest working temperature $T_{min}$ (Celsius degrees)
$Q_{max}$: the upper limit of the sample gas flow rate (litter/min).

6. An ultrasonic apparatus according to claim 1 wherein the conduit includes a straight portion and perpendicular portions perpendicularly connected to the ends of the straight portion;
the first and second ultrasonic transmission-reception devices are disposed in the perpendicular portions to face the ends of the straight portion; and
the distance between the first and second ultrasonic transmission-reception devices and the respective ends of the straight portion of the conduit satisfying the following relation $$0<D<f\pi r^2/C$$

D: the distance (m) between the first and second ultrasonic transmission-reception devices and the respective ends of the straight portion
f: frequency of the ultrasonic waves in the sample gas (Hz)
r: inner radius of the conduit (m)
C: velocity of the ultrasonic waves (m/sec).

7. A method of measuring the concentration of sample gas flowing through a conduit, comprising the steps of:

generating forward ultrasonic waves relative to the flow direction of the sample gas;

generating backward ultrasonic waves relative to the flow direction of the sample gas;

measuring the temperature of the sample gas flowing through the conduit;

generating trigger signals when the forward and backward waveforms pass over a predetermined level;

generating forward and backward zero-cross signals when the forward and backward waveforms pass over a zero level;

calculating a possible propagation time range on the basis of the gas temperature detected by the temperature sensor;

determining whether or not the phases at which two first trigger signals, respectively generated on the basis of the forward and backward waveforms, coincide with each other;

processing the zero-cross signals so that the phases coincide with each other if they do not coincide with each other;

obtaining reference zero-cross time instant by calculating mean value of the forward and backward zero-cross time instants;

obtaining an ultrasonic reception point by subtracting an integral multiple of the cycle of the ultrasonic waves so that the results of the subtraction falls into the possible propagation time range; and estimating the ultrasonic propagation time on the basis of the ultrasonic reception point.

8. A method according to claim 7 wherein the forward and backward ultrasonic waves are transmitted and received by first and second ultrasonic transmission-reception devices which are disposed in the conduit, the distance along the conduit between first and second ultrasonic transmission-reception devices being selected so that only one result of the subtraction falls into the possible propagation time range determined over possible working conditions of the ultrasonic apparatus.

9. A method according to claim 8 wherein the distance along the conduit between first and second ultrasonic transmission-reception devices is sleeted to satisfy the following relation $(L_s/C_{min}(T_{min})-L_s C_{max}(T_{min}))<1/f$ where:
f: frequency of the ultrasonic waves in the sample gas
$C_{min}(T_{min})$: the lower limit of the ultrasonic velocity (m/sec) through the sample gas at the lowest working temperature $T_{min}$ (Celsius degrees)
$C_{max}(T_{min})$: the upper limit of the ultrasonic velocity (m/sec) through the sample gas at the lowest working temperature $T_{min}$ (Celsius degrees).

10. A method according to claim 7 wherein the inner radius of the conduit is selected so that the difference between the forward and backward propagation time is smaller than the cycle of the ultrasonic waves under the working condition of the sample gas.

11. A method according to claim 7 wherein the inner radius of the conduit is selected to satisfy the following relation $L_s/(C_{min}(T_{min})-Q_{max}/(60000\pi r^2))$ $-L_s/(C_{min}(T_{min})+Q_{max}/(60000\pi r^2))<1/f$ where:
$L_s$: propagation length (m)
R: inner radius of the conduit (m)
f: frequency of the ultrasonic waves in the sample gas
$C_{min}(T_{min})$: the lower limit of the ultrasonic velocity (m/sec) through the sample gas at the lowest working temperature $T_{min}$ (Celsius degrees)
$Q_{max}$: the upper limit of the sample gas flow rate (litter/min).

12. An oxygen concentration system for generating an oxygen enriched gas, comprising
an oxygen concentration apparatus for generating an oxygen enriched gas by adsorbing nitrogen to remove the nitrogen from the air; and
an ultrasonic apparatus for measuring the concentration of the oxygen in the oxygen enriched gas and flow rate of the oxygen enriched gas, the ultrasonic apparatus comprising:
a conduit for receiving and flowing the oxygen enriched gas;
a first ultrasonic transmission-reception device mounted to the inside of the conduit;
a second ultrasonic transmission-reception device mounted to the inside of the conduit to face the first ultrasonic transmission-reception device;
a transmission-reception switch for switching the operation mode of the first and second ultrasonic transmission-reception devices between a transmission mode for transmitting ultrasonic waves and a reception mode for receiving ultrasonic waves;
a temperature sensor, disposed in the conduit, for measuring the temperature of the oxygen enriched gas flowing through the conduit;
the first ultrasonic transmission-reception device generating forward ultrasonic waves relative to the flow direction of the oxygen enriched gas when the device is in the transmission mode and generating backward waveform when the device is in the reception mode on the basis of the received ultrasonic waves generated by the second ultrasonic transmission-reception device;
the second ultrasonic transmission-reception device generating backward ultrasonic waves relative to the flow direction of the oxygen enriched gas when the device is in the transmission mode and generating forward waveform when the device is in the reception mode on the basis of the received ultrasonic waves generated by the first ultrasonic transmission-reception device;
means for generating trigger signals when the forward and backward waveforms pass over a predetermined level;
means for generating forward and backward zero-cross signals when the forward and backward waveforms pass over a zero level;
propagation time calculation means, coupled to the temperature sensor, the trigger signal generating means and the zero-cross signal generating means, for (1) calculating a possible propagation time range on the basis of the gas temperature detected by the temperature sensor, (2) determining whether or not the phases at which two first trigger signals, respectively generated on the basis of the forward and backward waveforms, coincide with each other, (3) processing the zero-cross signals so that the phases coincide with each other if they do not coincide with each other, (4) obtaining reference zero-cross time instant by calculating mean value of the forward and backward zero-cross time instants, (5) obtaining an ultrasonic reception point by subtracting an integral multiple of the cycle of the ultrasonic waves so that the results of the subtraction falls into the possible propagation time range and (6) estimating the ultrasonic propagation time on the basis of the ultrasonic reception point.

13. An oxygen concentration system according to claim 12 wherein the distance along the conduit between first and second ultrasonic transmission-reception devices is selected so that only one result of the subtraction falls into the possible propagation time range determined over possible working conditions of the ultrasonic apparatus.

14. An oxygen concentration system according to claim 13 wherein the distance along the conduit between first and second ultrasonic transmission-reception devices is sleeted to satisfy the following relation $$(L_s C_{min}(T_{min}) - L_s / C_{max}(T_{min})) < 1/f$$

where:
$L_s$: propagation length (m)
f: frequency of the ultrasonic waves in the sample gas
$C_{min}(T_{min})$: the lower limit of the ultrasonic velocity (m/sec) through the oxygen enriched gas at the lowest working temperature $T_{min}$ (Celsius degrees)
$C_{max}(T_{min})$: the upper limit of the ultrasonic velocity (m/sec) through the oxygen enriched gas at the lowest working temperature $T_{min}$ (Celsius degrees).

15. An oxygen concentration system according to claim 12 wherein the inner radius of the conduit is selected so that the difference between the forward and backward propagation time is smaller than the cycle of the ultrasonic waves under the working condition of the oxygen enriched gas.

16. An oxygen concentration system according to claim 12 wherein the inner radius of the conduit is selected to satisfy the following relation $$L_s/(C_{min}(T_{min}) - Q_{max}/(60000\pi r^2))$$

$$-L_s/(C_{min}(T_{min}) + Q_{max}/(60000\pi r^2)) < 1/f$$

where:
$L_s$: propagation length (m)
R: inner radius of the conduit (m)
f: frequency of the ultrasonic waves in the sample gas
$C_{min}(T_{min})$: the lower limit of the ultrasonic velocity (m/sec) through the oxygen enriched gas at the lowest working temperature $T_{min}$ (Celsius degrees)
$Q_{max}$: the upper limit of the oxygen enriched gas flow rate (litter/min).

17. An oxygen concentration system according to claim 12 wherein the conduit includes a straight portion and perpendicular portions perpendicularly connected to the ends of the straight portion;
the first and second ultrasonic transmission-reception devices are disposed in the perpendicular portions to face the ends of the straight portion; and
the distance between the first and second ultrasonic transmission-reception devices and the respective ends of the straight portion of the conduit satisfying the following relation $$0 < D < fxr^2/C$$

D: the distance (m) between the first and second ultrasonic transmission-reception devices and the respective ends of the straight portion f: frequency of the ultrasonic waves in the sample gas (Hz)
r: inner radius of the conduit (m)
C: velocity of the ultrasonic waves (m/sec).

18. An oxygen concentration system according to claim 12 wherein the conduit is secured to the oxygen concentration apparatus at one point to allow the conduit to thermally expand in the longitudinal direction of the straight portion freely from external force which may be generated when the conduit is thermally deformed.

19. An oxygen concentration system for generating an oxygen enriched gas, comprising:
an oxygen concentration apparatus for generating an oxygen enriched gas by adsorbing nitrogen to remove the nitrogen from the air; and
an ultrasonic apparatus for measuring the concentration of the oxygen in the oxygen enriched gas and flow rate of the oxygen enriched gas, the ultrasonic apparatus comprising:
a conduit for flowing an objective gas, the concentration of which is to be measured;
a first ultrasonic transmission-reception device mounted to the inside of the conduit;
a second ultrasonic transmission-reception device mounted to the inside of the conduit to face the first ultrasonic transmission-reception device;
the conduit includes a straight portion and perpendicular portions perpendicularly connected to the ends of the straight portion;
the first and second ultrasonic transmission-reception devices are disposed in the perpendicular portions to face the ends of the straight portion; and
the distance between the first and second ultrasonic transmission-reception devices and the respective ends of the straight portion of the conduit satisfying the following relation $$0 < D < fxr^2/C$$

where:
D: the distance (m) between the first and second ultrasonic transmission-reception devices and the respective ends of the straight portion
f: frequency of the ultrasonic waves in the sample gas (Hz)
r: inner radius of the conduit (m)
C: velocity of the ultrasonic waves (m/sec).

20. An oxygen concentration system according to claim 19 wherein the inner diameter of the straight portion is smaller than the outer diameter of first and second ultrasonic transducers.

21. An oxygen concentration system according to claim 19 wherein the conduit is secured to the oxygen concentration apparatus by means for allowing the longitudinal deformation of the straight portion freely from external force which may be generated when the conduit is thermally deformed.

22. An oxygen concentration system according to claim 19 wherein the conduit is secured to the oxygen concentration apparatus at one point to allow the conduit to thermally expand in the longitudinal direction of the straight portion freely from external force which may be generated when the conduit is thermally deformed.

* * * * *